United States Patent [19]

Wu

[11] Patent Number: 5,387,510
[45] Date of Patent: Feb. 7, 1995

[54] DETECTION OF AMPLIFIED NUCLEIC ACID USING SECONDARY CAPTURE OLIGONUCLEOTIDES AND TEST KIT

[75] Inventor: Annie L. Wu, Penfield, N.Y.

[73] Assignee: Eastman Kodak Company, Rochester, N.Y.

[21] Appl. No.: 769,624

[22] Filed: Oct. 2, 1991

[51] Int. Cl.$^6$ .................. C12Q 1/68; C07H 17/00; C12P 19/34

[52] U.S. Cl. ........................... 435/91.2; 435/6; 435/810; 435/91.5; 435/91.1; 536/23.1; 536/24.3; 536/24.32; 536/24.33; 935/16; 935/76; 935/77; 935/78; 935/88

[58] Field of Search ................ 435/91, 6, 91.1, 91.5, 435/91.2, 810; 536/24.32, 24.33, 24.3, 23.1; 935/16, 76, 77, 78, 88

[56] References Cited

U.S. PATENT DOCUMENTS

| | | | |
|---|---|---|---|
| 4,755,458 | 7/1988 | Rabbani et al. | 435/5 |
| 4,965,188 | 10/1990 | Mullis et al. | 435/6 |
| 5,079,351 | 1/1992 | Sainsky et al. | 536/27 |

FOREIGN PATENT DOCUMENTS 2202328 9/1988 United Kingdom ........... C12Q 1/68

Primary Examiner—Margaret Parr
Assistant Examiner—Bradley L. Sisson
Attorney, Agent, or Firm—J. Lanny Tucker

[57] ABSTRACT

A target nucleic acid can be amplified and detected using a water-insoluble capture probe having a short oligonucleotide (15–20 nucleotides) covalently attached to a polymeric particle, and one or more secondary oligonucleotides. The capture probe and secondary oligonucleotides are complementary to the target nucleic acid, although the sequences of complementarity are different. Moreover, each of the secondary oligonucleotides has a length which is equal to or greater than the length of the capture probe oligonucleotide. The secondary oligonucleotides are hybridized to the target nucleic acid either before or during hybridization of the target to the capture probe. The result is improved hybridization efficiency of capture probe and target nucleic acid.

17 Claims, No Drawings

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 17 nucleotides
        ( B ) TYPE: Nucleic acid
        ( C ) STRANDEDNESS: Single
        ( D ) TOPOLOGY: Linear ( i i ) MOLECULE TYPE: Probe oligonucleotide ( i i i ) HYPOTHETICAL: No ( i v ) ANTI-SENSE: No ( v i ) ORIGINAL SOURCE: Synthetically prepared ( v i i ) IMMEDIATE SOURCE: Synthetically prepared ( x ) PUBLICATION INFORMATION: None ( x i ) SEQUENCE DESCRIPTION: SEQ ID NO:1:

GCCTGATGCC GAGTACT                17

( 2 ) INFORMATION FOR SEQ ID NO:2:

( i ) SEQUENCE CHARACTERISTICS:
        ( A ) LENGTH: 30 nucleotides
        ( B ) TYPE: Nucleic acid
        ( C ) STRANDEDNESS: Single
        ( D ) TOPOLOGY: Linear ( i i ) MOLECULE TYPE: Primer ( i i i ) HYPOTHETICAL: No ( i v ) ANTI-SENSE: No ( v i ) ORIGINAL SOURCE: Synthetically prepared ( v i i ) IMMEDIATE SOURCE: Synthetically prepared ( x ) PUBLICATION INFORMATION: None ( x i ) SEQUENCE DESCRIPTION: SEQ ID NO:2:

CTCGGATCCG CATGTGCTAC TTCACCAACG      30

( 2 ) INFORMATION FOR SEQ ID NO:3:

( i ) SEQUENCE CHARACTERISTICS:
        ( A ) LENGTH: 27 nucleotides
        ( B ) TYPE: Nucleic acid
        ( C ) STRANDEDNESS: Single
        ( D ) TOPOLOGY: Linear ( i i ) MOLECULE TYPE: Primer ( i i i ) HYPOTHETICAL: No ( i v ) ANTI-SENSE: No ( v i ) ORIGINAL SOURCE: Synthetically prepared ( v i i ) IMMEDIATE SOURCE: Synthetically prepared ( x ) PUBLICATION INFORMATION: None ( x i ) SEQUENCE DESCRIPTION: SEQ ID NO:3:

```
        GAGCTGCAGG TAGTTGTGTC TGCACAC       27
```

( 2 ) INFORMATION FOR SEQ ID NO:4:

( i ) SEQUENCE CHARACTERISTICS:
        ( A ) LENGTH: 27 nucleotides
        ( B ) TYPE: Nucleic acid
        ( C ) STRANDEDNESS: Single
        ( D ) TOPOLOGY: Linear ( i i ) MOLECULE TYPE: Oligonucleotide ( i i i ) HYPOTHETICAL: No ( i v ) ANTI-SENSE: No ( v i ) ORIGINAL SOURCE: Synthetically prepared ( v i i ) IMMEDIATE SOURCE: Synthetically prepared ( x ) PUBLICATION INFORMATION: None ( x i ) SEQUENCE DESCRIPTION: SEQ ID NO:4:

```
        ACGTGGGGGT GTATCGGGCG GTGACGC       27
```

( 2 ) INFORMATION FOR SEQ ID NO:5:

( i ) SEQUENCE CHARACTERISTICS:
        ( A ) LENGTH: 26 nucleotides
        ( B ) TYPE: Nucleic acid
        ( C ) STRANDEDNESS: Single
        ( D ) TOPOLOGY: Linear ( i i ) MOLECULE TYPE: Oligonucleotide ( i i i ) HYPOTHETICAL: No ( i v ) ANTI-SENSE: No ( v i ) ORIGINAL SOURCE: Synthetically prepared ( v i i ) IMMEDIATE SOURCE: Synthetically prepared ( x ) PUBLICATION INFORMATION: None ( x i ) SEQUENCE DESCRIPTION: SEQ ID NO:5:

```
        GGAACAGCCA GAAGCAAGTC CTGGAG        26
```

DETECTION OF AMPLIFIED NUCLEIC ACID USING SECONDARY CAPTURE OLIGONUCLEOTIDES AND TEST KIT

FIELD OF THE INVENTION

This invention relates to a method for amplifying and detecting nucleic acids of interest It also relates to a test kit comprising a capture probe and secondary oligonucleotides useful for improved capture hybridization efficiency.

BACKGROUND OF THE INVENTION

Nucleic acid probe technology has developed rapidly in recent years as researchers have discovered its value for detection of various diseases, organisms or genetic features which are present in small quantities in a human or animal test sample. The use of probes is based upon the concept of complementarity such that complementary strands of nucleotides can and will, under proper conditions, hybridize to form a double stranded product. DNA inherently has two strands bound together by hydrogen bonds between complementary nucleotides (which are also known as nucleotide pairs). RNA, while being single stranded, also can hybridize with a complementary strand of nucleotides.

Hybridization of complementary strands is a central feature of what are known as hybridization assays (also known as genetic probe assays). Thus, if at least a sequence of a nucleic acid of interest (identified as a target nucleic acid) is known, it can be hybridized and detected using appropriate oligonucleotides (identified as probes) which are designed to be complementary to that known sequence. The probe usually is labeled in some fashion so that its detection also signals the presence of the hybridized product of probe and target nucleic acid. If the target nucleic acid is then unique to a particular organism, viral infection or genetic feature, the presence of the organism, virus or genetic feature can then readily be determined.

In some instances, the target nucleic acid (single strand form) is insolubilized on a solid surface (such as a nitrocellulose membrane) to prevent undesirable hybridization with oligonucleotides other than probes. Detection of the immobilized target nucleic acid can be accomplished using a detection probe specific for the target nucleic acid. Some have pointed out the disadvantages of such systems, for example EPA-0 318 245 (published May 31, 1989).

In what are known as "immunometric" or "sandwich" assays, the target nucleic acid may be captured using another oligonucleotide which is immobilized in some manner, for example on a membrane as described in U.S. Pat. No. 4,727,019 (issued Feb. 23, 1988). In other instances, the oligonucleotide is immobilized on polymeric particles which are embedded within a porous matrix (for examples as described in EP-A-0 200 381, published Nov. 5, 1986). The immobilized oligonucleotide is sometimes identified as a capture probe meaning that it "captures" the target nucleic acid so that it can be separated from undesirable materials which might obscure its detection. Once separation is accomplished, detection of the captured target nucleic acid can be achieved using a suitable procedure.

It is well known to attach oligonucleotides to particulate materials in hybridization assays and for purification of nucleic acids. EPA-0 200 133 (published Nov. 5, 1986), for example, describes the attachment of oligonucleotides to water-insoluble particles less than 50 micrometers in diameter for use in hybridization assays. Various linking groups for attaching nucleic acids to glass, polystyrene and latex particles are described in WO 88/01302 (published Feb. 25, 1988). This reference also mentions the use of dextran sulfate or a "nonhomologous" nucleic acid to treat the capture probe prior to its use to increase capture efficiency. A "nonhomologous" nucleic acid is defined as one that is "inert" which is believed to mean that it is not complementary to the probe oligonucleotide.

EP-A-0 318 245 (noted above) describes the need to improve the kinetics of hybridization between a water-soluble probe (such as a detection probe) and a long target nucleic acid in solution hybridization assays. This need is allegedly met using "helper" oligonucleotides which, it is believed, reorder the secondary and tertiary structure of the target nucleic acid in solution. These oligonucleotides hybridize with the target nucleic acid in regions other than that where the detection probe hybridizes.

Where a capture probe is used in a hybridization assay, the oligonucleotide attached to a water-insoluble support (such as a small polymeric particle) is usually very small in relation to the size of the support. The length of the oligonucleotide is so short that it extends only a very short distance from the surface of the support. Thus, steric hindrance is believed responsible for slow hybridization rates between the capture probe and the target nucleic acid.

One technique for solving this problem is described in U.S. Ser. No. 197,000 (filed May 20, 1988 by Saiki et al), abandoned. Improved hybridization is apparently achieved by inserting a polyribonucleotide or polydeoxyribonuecleotide spacer group between the support and the short capture oligonucleotide to extend the oligonucleotide away from the support surface.

Thus, there is a continuing need to improve the hybridization efficiency between target nucleic acids and insolubilized capture probes having very short oligonucleotides.

SUMMARY OF THE INVENTION

The present invention provides a way to improve hybridization of relatively short target nucleic acids with relatively short capture probes which are covalently bound to water-insoluble supports.

In one aspect, the present invention comprises a method for the amplification and detection of a double-stranded nucleic acid comprising:

A. after denaturation of a target double-stranded nucleic acid, and under hybridizing conditions, amplifying the target nucleic acid using a thermostable DNA polymerase, complementary primers and dNTPs, B. forming a water-insoluble hybridization product of the amplified target nucleic acid with a water-insoluble capture probe which is not detectably labeled, the capture probe comprising a water-insoluble polymeric particle to which is covalently attached an oligonucleotide complementary to a first sequence of the target nucleic acid, the oligonucleotide being from 15 to 20 nucleotides in length, and simultaneously or prior to such product formation, contacting the amplified target nucleic acid with one or more water-soluble, distinct secondary oligonucleotides, each of the secondary oligonucleotides being complementary to a sequence of the target nucleic acid other than the first sequence, and each of the secondary oligonucleotides having a length which is equal to or greater than the length of the capture probe oligonucleotide, to hybridize the secondary oligonucleotides with the amplified target nucleic acid, and C. detecting the resulting hybridized product of the target nucleic acid with the capture probe.

The invention also provides a kit for the amplification and detection of a target nucleic acid comprising:

a. a water-insoluble capture probe which is not detectably labeled and which comprises a water-insoluble polymeric particle to which is covalently attached an oligonucleotide complementary to a first sequence of the target nucleic acid, the oligonucleotide being from 15 to 20 nucleotides in length, and b. one or more water-soluble, distinct secondary oligonucleotides, each of the secondary oligonucleotides being complementary to a sequence of the target nucleic acid other than the first sequence, and each of the secondary oligonucleotides having a length which is equal to or greater than the length of the capture probe oligonucleotide.

The method and kit of this invention provides a means for rapid and sensitive detection of nucleic acids using known PCR procedures which are hereby improved in the detection step. The improvement is achieved by using secondary oligonucleotides with the capture probe, all of which hybridize with the amplified target nucleic acid. In addition, the assay provides advantages whereby the capture probe is readily separated from unwanted materials because of the polymeric particles to which the capture oligonucleotide is covalently and directly attached. Separation can be readily achieved using filtration membranes, porous matrices, centrifugation and other separation techniques. In addition, the capture probe can be attached in a suitable fashion to a nonporous particle which is readily contacted with an amplified target.

It is also important in this invention that the secondary oligonucleotides be of a certain length, namely equal to or greater than the length of the capture oligonucleotide. The capture oligonucleotide is from 15 to 20 nucleotides in length. This invention provides improved hybridization rates between target nucleic acid and capture probe. While not being bound to a specific theory, it is believed that the secondary oligonucleotides are minimally repulsed by the polymeric particle surface, thereby facilitating association of the target nucleic acid with the capture probe oligonucleotide.

DETAILED DESCRIPTION OF THE INVENTION

The general principles and conditions for amplification and detection of nucleic acids using polymerase chain reaction are quite well known, the details of which are provided in numerous references including U.S. Pat. No. 4,683,195 (issued Jul. 28, 1987 to Mullis et al), U.S. Pat. No. 4,683,202 (issued Jul. 28, 1987 to Mullis) and U.S. Pat. No. 4,965,188 (issued Oct. 23, 1990 to Mullis) and by Guatelli et al, *Clin. Microbiol. Rev,*, 2(2), pp. 217–226 (1989). Thus, many of the details of such technology are not included herein. However, in view of the teaching in the art and the specific teaching provided herein, a worker skilled in the art should have no difficulty in practicing the present invention by making the adjustments taught herein to accomplish the advantages noted herein.

The present invention is directed to the amplification and detection of one or more specific nucleic acid sequences present in one or more targeted nucleic acids in a test specimen. Such specimens can include cellular or viral material, hair, body fluids or other materials containing genetic DNA or RNA which can be detected.

The present invention is especially useful for producing, in exponential quantities relative to the number of reaction steps involved, at least one specific nucleic acid sequence. The product will be a discrete nucleic acid duplex with termini corresponding to the ends of the specific primers employed. Any source of nucleic acid, purified or not, can be utilized as the starting material if it is known to or suspected of containing the specific nucleic acid sequence targeted for detection. A mixture of nucleic acids can be employed if desired. The sequence to be duplicated can be a fragment of the entire nucleic acid. Moreover, a plurality of double stranded nucleic acids can be amplified and detected simultaneously by using a corresponding set of primers and detection means for each specific nucleic acid. Multiple sequences in the same nucleic acid can also be amplified and detected.

Nucleic acids to be detected can be obtained from various sources including plasmids, naturally occurring DNA or RNA from any source (such as bacteria, yeast, viruses, plants and higher animals, humans). It may be extracted from various tissues including blood, peripheral blood mononuclear cells (PBMC), tissue material or other sources known in the art using known procedures. The present invention is particularly useful for the amplification and detection of nucleic acid sequences found in genomic DNA, bacterial DNA, fungal DNA, viral RNA, or DNA or RNA found in bacterial or viral infected cells. This invention is most useful for the amplification and detection of fragments of DNA or RNA in human specimens, such fragments resulting from lysis or other disruptive procedures that break the original nucleic acid strand or strands.

The method described herein can be used to provide the detection or characterization of specific nucleic acid sequences associated with infectious diseases, genetic disorders or cellular disorders such as cancers. It may also be used in forensic investigations and DNA typing. For purposes of this invention, genetic diseases include specific deletions or mutations in genomic DNA from any organism, such as sickle cell anemia, cystic fibrosis, α-thalessemia, β-thalessemia and others readily apparent to one skilled in the art. Human Leukocyte Antigen (HLA) can be categorized with the present invention. Various infectious diseases can be diagnosed by the presence in a clinical sample of small quantities of specific DNA sequences characteristic of the organism, whether it be a yeast, bacterium or virus. Such bacteria which can be detected include, but are not limited to, Salmonella, Streptococcal organisms, Chlamydial organisms, Gonococcal organisms, *MyCobacterium tuberculosis*, *Mycobacterium avium* complex, *Mycoplasma Haemophilus influenzae*, Shigella and Listeria. Viruses which are detectable include, but are not limited to, herpes, Epstein Barr virus, cytomegalovirus, human papilloma virus, hepatitis and retroviruses such as HTLV-I, HIV-I and HIV-IF. Other detectable species would be readily apparent to one skilled in the art. The amount of β-globin DNA can also be detected. The invention is particularly useful for the detection of the presence of viral DNA.

Preferably, the target nucleic acid is less than 250-mer in length. The term "mer" is used to refer to a single nucleotide.

As used herein in referring to primers, probes, or secondary oligonucleotides, the term "oligonucleotide" refers to a molecule comprised of two or more deoxyribonucleotides or ribonucleotides, and preferably more than three. Its exact size is not critical (except as noted herein), but the size depends upon many factors including the ultimate use or function of the oligonucleotide. The oligonucleotide may be derived synthetically, by cloning or by other methods known in the art.

The term "primer" refers to an oligonucleotide, whether naturally occurring or synthetically produced, which is capable of acting as a point of initiation of synthesis when placed under conditions in which synthesis of a primer extension product complementary to a nucleic acid strand (that is, template) is induced. Such conditions include the presence of nucleotides (such as the four standard deoxyribonucleoside-5'-triphosphates) and an agent for polymerization such as a DNA polymerase, and suitable temperature, pH and cofactors.

The primer is preferably single stranded for maximum efficiency in amplification, but contain a double stranded region if desired as long as priming and extension are not inhibited. Preferably, the primer is an oligodeoxyribonucleotide. The exact size of each primer will vary depending upon the use contemplated, the complexity of the targeted sequence, reaction temperature and the source of the primer. Generally, the primers used in this invention will have from 12 to 60 nucleotides, and preferably, they have from 18 to 45 nucleotides.

In the practice of this invention, any of the primers used can contain a double-stranded, labeled nucleic acid region adjacent to a single-stranded region as described in U.S. Ser. No. 076,394 (filed Jul. 22, 1987 by Watson et al), abandoned.

The primers used in the present invention are selected to be "substantially complementary" to the different strands of each specific sequence to be amplified. This means that they must be sufficiently complementary to hybridize with their respective strands to form the desired hybridized products and then be extendable by a DNA polymerase. In the preferred and most practical situation, the primer has exact complementarity to the target nucleic acid. However, in many situations, exact complementarity is not possible or likely, and one or more mismatches may exist which do not prevent hybridization or the formation of primer extension products using the DNA polymerase.

In some situations where mismatches between the targeted nucleic acid and a primer are suspected, the effect of the mismatch may be overcome using specialized primer compositions, such as those described for example in EP-A-0 393 743 (published Oct. 24, 1990) and EP-A-0 417 842 (published Mar. 20, 1991).

Primers, probe oligonucleotides and secondary oligonucleotides useful herein can be obtained from a number of sources or prepared using known techniques and equipment, including for example, an ABI DNA Synthesizer (available from Applied Biosystems) or a Biosearch 8600 Series or 8800 Series Synthesizer (available from Milligen-Biosearch, Inc.) and known methods for their use (for example as described in U.S. Pat. No. 4,965,188, noted above). Naturally occurring primers isolated from biological sources are also useful (such as restriction endonuclease digests). As used herein, the term "primer" also refers to a mixture of primers such as may be used to detect targeted nucleic acids which may vary from specimen to specimen, or which may be used to overcome suspected mismatches between a primary primer and the template.

As used herein, a "capture probe" is a water-insoluble material comprised of a solid polymeric particle (described below) to which is covalently attached an oligonucleotide which is substantially complementary to a "first" nucleic acid sequence of the targeted nucleic acid.

The oligonucleotide of the probes is of a critical length, that is from 15 to 20 nucleotides, in order to best detect single base mutations or deletions in a target nucleic acid.

A "thermostable DNA polymerase", as is known in the art, is an enzyme which will function to accomplish the synthesis of primer extension products, and which is stable to heat, especially the high temperatures used for denaturation of DNA strands. More particularly, the thermostable DNA polymerases must not be substantially inactivated at the high temperatures used in polymerase chain reactions as described herein. Such temperatures will vary depending upon a number of reaction conditions, including pH, the nucleotide composition of the targeted nucleic acid and primers, the length of primer, salt concentration and other conditions known in the art and will be in the ranges noted below.

A number of thermostable DNA polymerases have been reported in the art, including those mentioned in detail in U.S. Pat. No. 4,965,188 (noted above) and U.S. Pat. No. 4,889,818 (issued Dec. 26, 1989 to Gelfand et al). Particularly useful polymerases are those obtained from various Thermus bacterial species, such as *Thermus aquaticus*, *Thermus thermophilus* or *Thermus flavus*. Other useful thermostable polymerases are described in WO-A-89/06691 (published Jul. 27, 1989). Some useful polymerases are commercially available. A number of techniques are known for isolating naturally-occurring thermostable polymerases from organisms, and for producing genetically engineered enzymes using recombinant techniques, as noted in the art cited in this paragraph.

Synthesis of extension products is initiated at the 3' end of each primer and proceeds in the 5' to 3' direction of the newly synthesized strand (or in the 3' to 5' direction of the template) until synthesis is terminated.

The secondary oligonucleotides used in the practice of this invention generally have a length equal to or greater than that of the probe oligonucleotide. More specifically, the length is from 15 to 35 nucleotides. At least one secondary oligonucleotide is used in the invention, each of which is complementary to a distinct sequence of the target nucleic acid, and those distinct sequences are different from the "first" sequence to which the probe oligonucleotide is complementary.

A targeted nucleic acid (that is, one to be amplified or detected) can be obtained from any of a variety of sources as noted above. Generally, it is extracted in some manner to make it available for contact with the primers and other reaction materials. This usually means removing unwanted proteins and cellular matter from the specimen in a suitable manner. Various procedures are known in the art, including those described by Laure et al in *The Lancet,* pp. 538-540 (Sept. 3, 1988), Maniatis et al, *Molecular Cloning: A Laboratory Manual,* pp. 280-281 (1982), Gross-Belland et al in *Eur. J.Biochem.,* 36, 32 (1973) and U.S. Pat. No. 4,965,188 (noted above). Extraction of DNA from whole blood or components thereof are described, for example, in EP-A-0 393 744 (published Oct. 24, 1990), Bell et al, *Proc, Natl. Acad. Sci. USA,* 78(9), pp. 5759-5763 (1981) and Saiki et al, *Bio/Technology,* 3, pp. 1008-1012 (1985).

Since the nucleic acid to be amplified or detected is usually in double stranded form, the two strands must be separated (that is, denatured before priming can take place). This can occur during the extraction process, or be a separate step afterwards. Denaturing is accomplished using a heat treatment alone or in combination with any suitable other physical, chemical or enzymatic means as described in the art. Heating alone to a suitable temperature is a preferred means.

The denatured strands are then cooled to a second temperature which is generally in the range of from about 55° to about 70° C. Once the denatured strands are cooled, priming and primer extension are carried out in the presence of the DNA polymerization reagents identified below. The resulting double-stranded primer extension products are heated to denature the strands. Once the strands are separated, they are available as templates for forming additional primer extension products therewith.

The specimen is mixed with the thermostable DNA polymerase, suitable deoxyribonucleotide-5'-triphosphates (dATP, dCTP, dGTP and dTTP) and a suitable set of primers at the beginning of the first cycle. The amount of thermostable DNA polymerase to be used is known in the art.

The dNTP's and primers are present in amounts effective for DNA polymerization to occur, such amounts being known in the art. Representative amounts are shown in the examples below. Other reagents are also preferably present, including salts such as magnesium chloride, extenders such as gelatin or other water soluble or water dispersible colloids. The reaction mixture is generally buffered to a pH of from about 7 to about 9 with pH of about 8 being preferred using any of a number of suitable buffers known in the art. The volume of the reaction mixture including the targeted nucleic acid is not critical, but with smaller volumes, heat can be transferred to and away more rapidly.

The reagents for polymerization can be added to the specimen containing targeted nucleic acid at any suitable time, as is known in the art. The reagents can be added at several and various times during an amplification cycle. Workers skilled in the art would be able to design an acceptable protocol for reagent addition.

The newly synthesized hybridized product of the template and its complementary nucleic acid formed from the primer are used in subsequent steps of the method. They are then denatured by heating, and used as templates for further cycles of priming, extension and denaturation as is known in the art. The time for each cycle can vary widely depending upon the equipment and reagents used. In a preferred embodiment, each cycle is about 120 seconds or less, as described in copending U.S. Ser. No. 693,574 (filed Apr. 30, 1991 by Findlay et al). The cycle can be completed as often as needed to produce the desired quantity of the targeted nucleic acid.

After the last cycle, the final primer extension products can be detected as described below. Preferably, the products are denatured a last time providing multiple copies of the strands of the targeted nucleic acid.

The amplification method of this invention is preferably conducted in a continuous, automated manner so that the reaction mixture is temperature cycled in a controlled manner for desired preset times. A number of instruments have been developed for this purpose, as one of ordinary skill in the art would know.

One such instrument for this purpose is described in some detail in U.S. Pat. No. 4,965,188 (noted above) and EP-A-0 236 069 (published Sep. 9, 1987), and involves moving liquids from one temperature environment to another under controlled conditions.

Another instrument utilizes temperature cycling without a liquid handling system, and is also described in some detail in U.S. Pat. No. 4,965,188 and EP-A-0 236 069 (noted above). Generally, this instrument includes a heat conducting container for holding a number of reaction tubes containing reaction mixture, a means for heating, cooling and temperature maintenance and a computing means to generate signals to control the amplification sequence, changes in temperature and timing.

A gas chromatograph has also been used for amplification, as described for example by Hoffman et al, *Biotechniques,* 6(10), pp. 932-936 (1988), and amplification in a "teacup" has been described as simple and inexpensive, Innis et al (Eds.), *PCR Protocols: A Guide to Methods and Applicants,* Chapter 51, pp. 429-434 by Robert Watson, Academic Press, Inc., 1990.

A preferred instrument for processing amplification reactions in a disposable chemical test pack is described in some detail in U.S. Ser. No. 452,666 (filed Dec. 18, 1989 by Devaney Jr. et al as a CIP of U.S. Ser. No. 365,079, filed Jun. 12, 1989, now abandoned). In general, this instrument comprises a support surface for supporting a chemical test pack, pressure applicators supported above the surface for acting on the reaction pack to transfer fluids between adjacent chambers in the test pack, and means for operating the pressure applicators through a range of movement extending across the test pack.

U.S. Ser. No. 452,932 (filed Dec. 18, 1989 by Devaney Jr. et al as a CIP of U.S. Ser. No. 365,079 filed Jun. 12, 1989, now abandoned) provides details of useful chemical test packs which can be processed using the instrument described in U.S. Ser. No. 452,666 (noted above), now U.S. Pat. No. 5,089,233. Also described therein are means for heating and cooling the test pack at repeated intervals (that is, through cycles) appropriate for the method of the present invention.

The method of this invention can be used to advantage to rapidly detect a target nucleic acid which is present, for example, in an infectious agent. Once a desired amount of the target nucleic acid has been generated, it is detected by forming a water-insoluble, hybridization product of it with a capture probe which is not labeled.

The capture probe comprises a water-insoluble polymeric particle to which is covalently attached an oligonucleotide (15-20 nucleotides) which is complementary to a first sequence of the target nucleic acid.

The oligonucleotide can be directly attached through covalent bonds resulting from chemical reaction of the oligonucleotide and reactive groups on the particles. Alternatively, a spacer group of some type can be attached to the particle or oligonucleotide prior to attachment. One such useful spacer group and procedures for its use are described in U.S. Pat. No. 4,914,210 (issued Apr. 3, 1990 to Levenson et al).

A wide variety of polymeric particles can be used in practicing this invention, including those prepared from naturally occurring or synthetically prepared polymers. Preferably the particles are spherical in shape and have an average size (largest dimension) of from about 0.01 to about 10 μmeters, although the size, structural and spatial configurations are not critical. Preferred particles have an average diameter of from about 0.01 to about 5 meters. Many such particles are commercially available from a number of sources. Alternatively, reagents and procedures for preparing such particles are well known, for example as described in EP-A-0 323 692 (published Jul. 12, 1989).

The oligonucleotide is covalently attached to the surface of the particles using any of a number of reactive groups and reactions known in the art. Reactive groups on the surface of the particles can be provided as part of the structure of the polymer, or added by coating or chemical treatment of an inert material. One skilled in the art would readily understand how to prepare such materials to have suitable reactive groups including, but not limited to: carboxy, 2-substituted ethylsulfonyl, 2-substituted ethylcarbonyl, vinylsulfonyl, amino, sulfhydryl, vinylcarbonyl, epoxy, aldehyde, active halogen groups, hydrazide and active esters such as succinimidoxycarbonyl.

Particularly useful particulate carrier materials are polymeric beads described, for example, in EP-A-0 323 692 (noted above) which are prepared from one or more ethylenically unsaturated polymerizable monomers having an active halogen group, activated 2-substituted ethylsulfonyl or vinylsulfonyl groups. Other particularly useful particles having reactive carboxy groups are described in copending U.S. Ser. No. 654,112 (filed Feb. 12, 1991 by Ponticello et al).

Useful homo- and copolymers include, but are not limited to: poly(styrene-co-acrylic acid) (70:30 molar ratio), poly(m & p-chloromethylstyrene), poly(styrene-co-m & p -chloromethylstyrene-co-2-hydroxyethyl acrylate) (67:30:3 molar ratio), poly[styrene-co-m & p2-(2-chloroethylsulfonyl-methyl)styrene] (96:4 molar ratio), poly{styrene-co -N-(m & p-(2-chloroethylsulfonylmethyl)phenyl]acrylamide}(99.3:0.7 molar ratio), poly(m & p-chloromethylstyrene-co-metharylic acid) (95:5 molar ratio), poly[styrene-co-m & p-(2-chloroethylsulfonylmethyl)styrene-co-methacrylic acid] (93.5:4.5:2 molar ratio) and poly[styrene-co-4-(2- chloroethylsulfonylmethyl)styrene] (95.5:4.5 molar ratio ).

Procedures for attaching oligonucleotides to particles having reactive groups are well known. Useful technology includes the procedures described in U.S. Ser. No. 471,168 (filed Jan. 26, 1990 by Warren III et al), now abandoned in favor of U.S. Ser. No. 847,447 (filed Mar. 6, 1992), U.S. Pat. No. 4,713,326 (issued Dec. 15, 1987 to Dattagupta et al), W)-A-88/01302 (published Feb. 25, 1988), EP-B-0 070 687 (published Jan. 26, 1983) and U.S. Pat. No. 4,914,210 (noted above).

Forming a hybridization product of the amplified target nucleic acid and the capture probe can be accomplished by mixing the two materials under conventional conditions, such as a temperature in the range of from about 40° to about 45° C. for a time of at least about 5 minutes. Representative specific conditions are described in the example below.

Simultaneously with or prior to the hybridization of the capture probe and target nucleic acid, the target nucleic acid is also hybridized with two or more distinct secondary oligonucleotides. Each of these oligonucleotides is complementary to a distinct sequence of the target nucleic acid which is different from the first sequence noted above, and different from each other. The length of these oligonucleotides is described above. They are generally unlabeled and water-soluble. Preferably two secondary oligonucleotides are used in the assay, but more can be used if desired. It is also preferred that the amplified target nucleic acid be contacted with the capture probe and secondary oligonucleotides substantially simultaneously. The amount of secondary oligonucleotide can be widely varied, but preferably it is present at about the same concentration as the capture probe oligonucleotide.

The resulting hybridized product of amplified target nucleic acid, capture probe and secondary oligonucleotides can be detected in any suitable fashion which would be apparent to a skilled worker in the art.

Generally, detection requires that the hybridized product be separated from the other materials in the reaction medium. This can be done by any of a number of ways, including filtration, centrifugation or other suitable separation techniques.

Particularly useful separation means include microporous filtration membranes such as the polyamide membranes marketed by Pall Corp. (for example as LOPRODYNE ™ or BIODYNE ™ microporous filtration membranes). They can be used uncoated or precoated with surfactants or other materials which facilitate fluid flow. Other types of filters can be used also.

The membranes or filters can be used as a separate article with suitable containers for collecting fluid and water-soluble materials. Preferably, however, the membranes are mounted as part of a test device. Various test devices are known in the art including those described in U.S. Pat. No. 3,825,410 (issued Jul. 23, 1974 to Bagshawe), U.S. Pat. No. 3,888,629 (issued Jun. 10, 1975 to Bagshawe), U.S. Pat. No. 3,970,429 (issued Jul. 20, 1976 to Updike) and US-A-4,446,232 (issued May 1, 1984 to Liotta). Particularly useful devices are described in U.S. Pat. No. 4,921,677 (issued May 1, 1990) and are commercially available as SURECELL ™ test devices and assay kits from Eastman Kodak Company.

Alternatively to separation as described above, the target nucleic acid can be detected using the capture probe which has been immobilized on a flat substrate, such as the microporous filtration membranes described above, or on thin polymeric films, uncoated papers or polymer coated papers, a number of which are known in the art, glass slides and other nonporous substrates readily apparent to one skilled in the art. Other details about using immobilized capture probes, for example in self-contained chemical test packs are provided in U.S. Ser. No. 571,560 (filed Sept. 4, 1990 as a CIP of, now abandoned U.S. Ser. No. 306,954 (filed Feb. 3, 1989 by Findlay et al, and corresponding to EP-A-0 408 738, published Jan. 23, 1991), abandoned, U.S. Pat. No. 4,902,624 (issued Feb. 20, 1990 to Columbus et al) and U.S. Ser. No. 452,932 (filed Dec. 18, 1989, now abandoned by Devaney Jr. et al as a CIP of U.S. Ser. No. 365,079 filed Jun. 12, 1989).

In one embodiment, detection of the hybridized product can be accomplished using a detection probe which is complementary either to the capture probe or to still another sequence of the target nucleic acid (that is, a sequence other than those complementary to the capture probe and secondary oligonucleotides).

In another embodiment, detection can be achieved using a detection probe complementary to at least one of the secondary oligonucleotides.

Procedures for attaching labels for detection and preparing such probes are well known in the art, for example, as described by Agrawal et al, *Nucleic Acid Res.*, 14, pp. 6227–45 (1986), U.S. Pat. No. 4,914,210 (issued Apr. 3, 1990 to Levenson et al) relating to biotin labels, U.S. Pat. No. 4,962,029 (issued Oct. 9, 1990 to Levenson et al) relating to enzyme labels, and the references noted therein. Useful labels include radioisotopes, electron-dense reagents, chromogens, fluorogens, phosphorescent moieties, ferritin and other magnetic particles (see U.S. Pat. No. 4,795,698 issued Jan. 3, 1989 to Owen et al and U.S. Pat. No. 4,920,061 issued Apr. 24, 1990 to Poynton et al), chemiluminescent moieties and enzymes (which are preferred). Useful enzymes include, glucose oxidase, peroxidases, uricase, alkaline phosphatase and others known in the art and can be attached to oligonucleotides using known procedures. Substrates and reagents for providing a detectable colorimetric, fluorometric or chemiluminescent signal in the presence of a given enzyme label are well known, for example as described in U.S. Pat. No. 4,994,373 (issued Feb. 19, 1991 to Stavrianopoulos et al).

Where the label is a preferred enzyme such as a peroxidase, at some point in the assay, hydrogen peroxide and suitable dye-forming compositions are added to provide a detectable dye. For example, useful dye-providing reagents include tetramethylbenzidine and derivatives thereof, and leuco dyes, such as triarylimidazole leuco dyes (as described in U.S. Pat. No. 4,089,747 issued May 16, 1978 to Bruschi), or other compounds which react to provide a dye in the presence of peroxidase and hydrogen peroxide. Particularly useful dye-providing compositions are described in EP-A-0 308 236 (published Mar. 22, 1989).

Detection of the resulting signal can be achieved using suitable detection equipment and procedures which are well known. Certain probes may provide signals which are visible to the eye without the use of detection equipment.

In a preferred embodiment, one of the primers is labeled with a specific binding ligand such as biotin, an antibody or lectin. The labeled primer provides (through amplification) an amplified target nucleic acid which has the specific binding ligand attached. This amplified nucleic acid is detected using a detectably labeled receptor for specific binding ligand. For example, if the specific binding moiety is biotin, the receptor is avidin or an equivalent thereof. The receptor, for example avidin, can be conjugated with an enzyme, or have a radioactive moiety which provides a detectable signal as noted above. Further details of this embodiment are described, for example, in U.S. Ser. No. 306,954 (noted above), now abandoned.

In still another embodiment, the amplified target nucleic acid can be detected by incorporating a radioisotope into the amplified product by using dNTPs in the primer extension which are labeled with a radioisotope.

It is also useful for the method of this invention to be carried out in a suitable container. The most crude container would be a test tube, cuvette, flask or beaker, but more sophisticated containers have been fashioned in order to facilitate automated procedures for performing the method. For example, a cuvette constructed to provide certain temperature characteristics during the practice of the method is described in U.S. Pat. No. 4,902,624 (as noted above).

The following examples are included to illustrate the practice of this invention, and are not meant to be limiting in any way. All percentages are by weight unless otherwise noted.

Examples 1–3;

Assay for HLA DNA

These examples illustrate the practice of this invention for the amplification and detection of a representative nucleic acid, namely a fragment of HLA DNA.

Materials and Methods

A capture probe was composed of particles of poly(s-tyrene-co-acrylic acid) (70:30 molar ratio, 2.1 μmeter average diameter) having covalently attached thereto an oligonucleotide having the following sequence which is complementary to a first sequence of the target nucleic acid:

SEQ ID NO:1: 5'-X-GCCTGATGCC GAGTACT-3'

The oligonucleotide was attached to the particles through "X", an aminotetraethylene glycol linker having 16 ethylene glycol units using the procedure described in U.S. Pat. No. 4,914,210 (noted above). More specifically, an aqueous suspension of the particles (1 ml, 30 mg solids) was centrifuged and the supernatant discarded. The particles were then resuspended in glass-distilled water (1 ml) by vigorous vortexing, followed by centrifugation and removal of the supernatant. The particles were then resuspended again in a solution (1 ml) of sodium chloride (3 normal) in methylimidazole buffer (0.2 molar, pH 7).

To this suspension was added the noted oligonucleotide (2.5 nmoles) followed by thorough mixing. The activating compound, 1-(3-dimethylaminopropyl)-3-ethylcarbodiimide hydrochloride (5 mg) was added, and after thorough mixing by vortex, the reaction mixture was incubated at room temperature with occasional stirring for at least two hours.

The reaction mixture was centrifuged and the supernatant removed. The resulting particulate reagent was washed with the following fluids by centrifugation and pipetting off the supernatant between washings: a) three washings with glass-distilled water (1 ml each time), and b) three washings with a buffer solution (1 ml each time, pH 7.4) comprising sodium chloride (0.018 molar), sodium phosphate (1 mmolar) ethylenediaminetetraacetic acid (0.1 mmolar) and dodecyl sulfate (0.5%) and which had been prewarmed to 70° C.

After the last wash, the reagents were resuspended in glass-distilled water to a final volume of 1 ml to make a 3% dispersion. It was stored at 4° C. until its use.

A leuco dye composition was prepared containing 2-(4-hydroxy-3,5-dimethoxyphenyl)-4,5-bis(4methoxyphenyl)imidazole as follows: Solid leuco dye (to make a 0.1% solution) was dissolved in a solution of poly(vinylpyrrolidone) (20%) in sodium phosphate buffer (5 mmolar). This solution was then added to a solution of hydrogen peroxide (10 mmolar), 4'-hydroxyacetanilide electron transfer agent (5 mmolar) and diethylenetriaminepentaacetic acid chelating agent (10 mmolar) in sodium phosphate buffer to produce a final concentration of 1% polymer and 0.005% leuco dye.

A DNA polymerase was used during amplification which was isolated from *Thermus aquaticus* using standard procedures, and which had an activity of about 4 units/μl). A "unit" is defined as the amount of enzyme activity required to incorporate 10 nmoles of total nucleotides (DNTP's) into an extending nucleic acid chain in 30 minutes at 74° C.

The target nucleic acid was a HLA DNA fragment generated by amplifying a 231-base pair segment of HLA DQB gene using primers flanking a hyperviable region located in Exon 1. The HLA DNA fragment was isolated from the cell line FPF (Human Genetic Mutant Cell Deposit, Camden, N.J.) as described by Maniatis et al, *Molecular Cloning, A Laboratory Manual*, page 458, Cold Spring Harbor Laboratory, New York, 1982.

An avidin-horseradish peroxidase conjugate was purchased from Sigma Chemical Co.

The primers used in amplification in the assay had the following sequences:

SEQ ID NO:2:

5'-Y-CTCGGATCCG CATGTGCTAC
TTCACCAACG-3' and
SEQ ID NO:3:
5'-GAGCTGCAGG TAGTTGTGTC TGCACAC-3'
wherein Y represents a biotintetraethylene glycol linker moiety attached to the oligonucleotide using the procedure described in U.S. Pat. No. 4,914,210 (noted above).

The secondary oligonucleotides used in the practice of this invention had the following sequences:
SEQ ID NO:4:

5'-ACGTGGGGGT GTATCGGGCG
GTGACGC-3'

SEQ ID NO:5:

5'-GGAACAGCCA GAAGCAAGTC
CTGGAG-3'

All of the oligonucleotides used in these examples were prepared and purified using a conventional automated SAM-1 DNA synthesizer (Biosearch) and known procedures (for example, as described by Beaucage et al, *Tetrahedron Letters*, 22, 1859-1862, 1981).

Assay Protocol

An amplified target nucleic acid was provided by amplifying the noted HLA DNA fragment using tritiated dNTP's in the following manner:

The HLA DNA fragment (1 μg) was added to a buffer solution (100 μl) containing tris(hydroxymethyl)aminomethane hydrochloride buffer (67 mmolar, pH 8.8), ammonium sulfate (16.6 mmolar), magnesium chloride (2.5 mmolar) and gelatin (10 μg). The primers described above were added (20 pmoles of each) followed by the tritiated dNTP's (0.17 mmolar of each), and the DNA polymerase (12 units).

Amplification was carried out for 35 of the following cycles using a conventional Perkin-Elmer Thermal Cycler:

denaturation at 95° C. for 30 seconds, cooling to and hybridization at 65° C. for 30 seconds, and heating to and primer extension at 70° C. for 1 minute.

A solution (10 μl) of the resulting amplified target nucleic acid was heated to 95° C. for five minutes to denature the strands of nucleic acid, then mixed separately with the following components:

the capture probe (150 μg) alone in a Control assay, the capture probe (150 μg) and secondary oligonucleotide SEQ ID NO: 4 (identified above, 50 μmolar) in Example 1, the capture probe (150 μg) and secondary. oligonucleotide SEQ ID NO: 5 (identified above, 50 Bmolar) in Example 2, and the capture probe (150 μg) and both secondary oligonucleotides SEQ ID NO: 4 and SEQ ID NO: 5 (identified above, 50 μmolar) in Example 3.

Each of the resulting suspensions were in a buffered solution containing sodium phosphate (0.125 molar, pH 6.8), sodium chloride (2.5 molar) and ethylenediaminetetraacetic acid (1 mmolar). They were incubated at 42° C. for 10 minutes to allow the capture and secondary oligonucleotides to hybridize to the amplified target nucleic acid.

The hybridized products were washed with a solution (300 μl) containing sodium phosphate (0.85 mmolar), sodium chloride (15 mmolar) and sodium dodecyl sulfate (0.5%) which had been prewarmed to 50° C. The resulting suspensions were centrifuged, and the supernatants decanted. The amount of tritium label remaining in the water-insoluble product was measured for all assays. The results are shown in Table I below.

A separate set of suspensions containing the hybridized products of capture probe, secondary oligonucleotides and amplified target nucleic acid were detected using colorimetric signals in SURECELL ™ disposable test devices (Eastman Kodak Company). These devices contained three test wells having a LOPRODYNE ™ microporous membrane (1.2 μmeter average pore size, Pall Corp.) in each test well. The suspensions were added to the test devices and fluid was allowed to flow through the membranes while retaining the hybridized products on the membranes.

The products were washed with a solution (300 μl) containing sodium phosphate (0.85 mmolar), sodium chloride (15 mmolar) and sodium dodecyl sulfate (0.5%) which had been prewarmed to 50° C.

The avidin-horseradish peroxidase conjugate (30 μl of solution containing 2.3 ng of conjugate) was added to the test wells, and the SURECELL ™ test devices were incubated at room temperature for 2 minutes. The products were then washed with a solution (200 μl) containing tris(hydroxymethyl)aminomethane (50 mmolar, pH 8.8), sodium dodecyl sulfate (2.4%), sodium chloride (0.5 molar) and 1-methyl-2-pyrrolidinone (0.25 mmolar). The leuco dye solution (50 μl) was added, followed by incubation for 5 minutes at room temperature. The dye signal on the membranes was visually evaluated and scored against a color chart (scores of 0 to 10 with 10 representing highest dye density). The results are shown in Table I below.

The results indicate that the presence of one or both of the secondary oligonucleotides improves the efficiency of detection of the amplified target nucleic acid.

TABLE 1

| Assay | Tritium Label Signal (counts per minute) | Visual Dye Signal |
|---|---|---|
| Control | 651 | 7.5 |
| Example 1 | 3296 | 10 |
| Example 2 | 2212 | 9 |

TABLE 1-continued

| Assay | Tritium Label Signal (counts per minute) | Visual Dye Signal |
| --- | --- | --- |
| Example 3 | 3291 | 10 |

The invention has been described in detail with particular reference to preferred embodiments thereof, but it will be understood that variations and modifications can be effected within the spirit and scope of the invention. All patents, patent applications (published or unpublished, domestic or foreign), scientific literature, books and other prior art cited herein are each incorporated herein by reference for the teaching therein pertinent to this invention.

I claim:

1. A method for amplification and detection of a double-stranded nucleic acid comprising:

A. after denaturation of a target double-stranded nucleic acid, amplifying said target nucleic acid using a thermostable DNA polymerase, complementary primers and dNTPs, B. forming a water-insoluble hybridization product of said amplified target nucleic acid with a water-insoluble capture probe which is not detectably labeled, said capture probe comprising a water-insoluble polymeric particle to which is covalently attached an oligonucleotide complementary and specific to a first sequence of said amplified target nucleic acid, said oligonucleotide being from 15 to 20 nucleotides in length, and simultaneously or prior to said product formation, contacting said amplified target nucleic acid with one or more water-soluble, unlabeled, distinct secondary oligonucleotides, each of said secondary oligonucleotides being complementary and specific to a sequence of said amplified target nucleic acid other than said first sequence, and each of said secondary oligonucleotides having a length which is equal to or greater than the length of said capture probe oligonucleotide, to hybridize said secondary oligonucleotides with said amplified target nucleic acid, and C. detecting the resulting hybridized product formed from said amplified target nucleic acid and said water-insoluble capture probe, said detection being accomplished in one of the following ways:

1) using a a detectably labeled detection probe which is commlementary and specific to said amplified target nucleic acid in a region thereof other than to which said capture probe and second secondary oligonucleotides hybridize, 2) using at least one detectably primer as one of said complementary primers in amplification stem A), or 3) using a detectably labeled dNTP in amplification Step A).

2. The method of claim 1 wherein said amplified target nucleic acid is contacted with said capture probe and said secondary oligonucleotides simultaneously.

3. The method of claim 1 wherein the concentration of said secondary oligonucleotides is about the same as that of said capture probe oligonucleotide.

4. The method of claim 1 wherein each hybridization is carried out at a temperature of from about 40° to about 45° C. for at least about 5 minutes.

5. The method of claim 1 wherein said target nucleic acid is less than 250-mer in length.

6. The method of claim 1 wherein said hybridized product is detect using a detection probe which is complementary and spsecific to said amplified target nucleic acid in a region thereof other than to which said capture probe and second secondary oligonucleotides hydridize.

7. The method of claim 1 wherein at least one of said primers is detectably labeled for detection of said hybridized product.

8. The method of claim 1 wherein said hybridized product is detected using a detection probe which is complementary and specific to one of said secondary oligonucleotides.

9. The method of claim 1 wherein amplification is achieved using a thermostable DNA polymerase isolated from a *Thermus* species, or a recombinant equivalent thereof, and at least 20 amplification cycles.

10. The method of claim 1 wherein said capture probe is immobilized on a substrate selected from the group consisting of a microporous filtration membrane, a polymeric film and a resin-coated paper, and detection of said hybridized product occurs on said substrate.

11. A kit for a combined process of the amplification and detection of a target nucleic acid consisting essentially of, in individual packaging:

a. a water-insoluble capture probe which is not detectably labeled and which comprises a water-insoluble polymeric particle to which is covalently attached an oligonucleotide complementary to a first sequence of said target nucleic acid, said oligonucleotide being from 15 to 20 nucleotides in length, b. one or more water-soluble, unlabeled, distinct secondary oligonucleotides, each of said secondary oligonucleotides, each of said secondary oligonucleotides being complementary and specific to a sequence of said target nucleic acid other than said first sequence, and each of said secondary oligonucleotides having a length which is equal to or greater than the length of said capture probe oligonucleotide, c. primers specific for said amplified target nucleic acid, d. a thermostable DNA polymerase, and e. dNTP's, wherein either one of said primers or said dNTP's is detectably labeled.

12. The kit of claim 11 wherein said particles have an average diameter of from about 0.1 to about 10 $\mu$meters.

13. The kit of claim 11 wherein said capture probe oligonucleotide is from about 15-mer to about 20mer, and each of said secondary oligonucleotides is independently from about 15-mer to about 35-mer.

14. The kit of claim 11 further including a disposable test device comprising a microporous membrane.

15. The kit of claim 14 wherein said capture probe is immobilized on said microporous membrane.

16. The kit of claim 1 wherein at least one of said primers is detectably labeled.

17. The kit of claim 16 wherein at least one of said primers is detectably labeled with biotin, and said kit further includes a composition for providing a colorimetric or chemiluminescent signal upon reaction with biotin, said composition comprising avidin conjugated with a detectable label which provides a colorimetric or chemluminescent signal.

* * * * *